(12) United States Patent
Hironaka et al.

(10) Patent No.: US 11,246,931 B2
(45) Date of Patent: Feb. 15, 2022

(54) ACTIVE PHARMACEUTICAL INGREDIENT CARRIER AND PRODUCTION METHOD OF THE SAME

(71) Applicant: Tokuyama Corporation, Shunan (JP)

(72) Inventors: Yoshimi Hironaka, Shunan (JP); Tadahiro Fukuju, Shunan (JP); Hiromasa Yamamoto, Shunan (JP)

(73) Assignee: Tokuyama Corporation, Shunan (JP)

( * ) Notice: Subject to any disclaimer, the term of this patent is extended or adjusted under 35 U.S.C. 154(b) by 62 days.

(21) Appl. No.: 16/614,286

(22) PCT Filed: May 17, 2018

(86) PCT No.: PCT/JP2018/019097
§ 371 (c)(1),
(2) Date: Nov. 15, 2019

(87) PCT Pub. No.: WO2018/212275
PCT Pub. Date: Nov. 22, 2018

(65) Prior Publication Data
US 2020/0147220 A1    May 14, 2020

(30) Foreign Application Priority Data

May 19, 2017 (JP) .............................. JP2017-100032
Feb. 9, 2018 (JP) .............................. JP2018-021540

(51) Int. Cl.
*A61K 47/02* (2006.01)
*C01B 33/12* (2006.01)

(52) U.S. Cl.
CPC .............. *A61K 47/02* (2013.01); *C01B 33/12* (2013.01); *C01P 2002/02* (2013.01); *C01P 2006/14* (2013.01); *C01P 2006/16* (2013.01)

(58) Field of Classification Search
None
See application file for complete search history.

(56) References Cited

U.S. PATENT DOCUMENTS

| 7,749,521 | B2 | 7/2010 | Martens et al. |
| 8,273,371 | B2 | 9/2012 | Martens et al. |
| 2005/0025690 | A1 | 2/2005 | Fukuda et al. |
| 2006/0134219 | A1 | 6/2006 | Martens et al. |
| 2008/0153694 | A1 | 6/2008 | Nishi et al. |
| 2009/0060816 | A1 | 3/2009 | Fukuda et al. |
| 2010/0008990 | A1 | 1/2010 | Martens et al. |
| 2010/0331177 | A1 | 12/2010 | Nishi et al. |
| 2011/0086099 | A9 | 4/2011 | Martens et al. |
| 2011/0244002 | A1 | 10/2011 | Shen et al. |
| 2013/0189521 | A1 | 7/2013 | Fukuju et al. |
| 2014/0336274 | A1 | 11/2014 | Maio et al. |
| 2016/0193588 | A1 | 7/2016 | Haynes et al. |
| 2016/0303048 | A1 | 10/2016 | Libanati et al. |
| 2017/0049892 | A1 | 2/2017 | Maio et al. |

FOREIGN PATENT DOCUMENTS

| JP | 2005089240 | A | 4/2005 |
| JP | 2006248832 | A | 9/2006 |
| JP | 2006248922 | A | 9/2006 |
| JP | 2012506904 | A | 3/2012 |
| JP | 2014522363 | A | 9/2014 |
| JP | 2016044091 | A | 4/2016 |
| WO | 2005000740 | A2 | 1/2005 |
| WO | 2005012175 | A1 | 2/2005 |
| WO | 2012/057086 | A1 | 5/2012 |
| WO | 2014078435 | A1 | 5/2014 |
| WO | 2017/188222 | A1 | 11/2017 |

OTHER PUBLICATIONS

Barrett, E. P., et al., The Determination of Pore Volume and Area Distributions in Porous Substances. I. Computations from Nitrogen Isotherms, Journal of the American Chemical Society, 1951, p. 373-380, vol. 73.

*Primary Examiner* — Jennifer Lamberski
(74) *Attorney, Agent, or Firm* — The Webb Law Firm (57) ABSTRACT

The present invention relates to an active pharmaceutical ingredient carrier and a production method of the same. The active pharmaceutical ingredient carrier includes silica having a volume of a pore with a pore radius of 1 to 100 nm determined by BJH method of 3.0 to 5.0 ml/g, and a peak of a pore radius of 10 to 50 nm determined by BJH method; and an active pharmaceutical ingredient carried by the silica.

5 Claims, 6 Drawing Sheets

ACTIVE PHARMACEUTICAL INGREDIENT CARRIER AND PRODUCTION METHOD OF THE SAME

CROSS-REFERENCE TO RELATED APPLICATIONS

This application is the United States national phase of International Application No. PCT/JP2018/019097 filed May 17, 2018, and claims priority to Japanese Patent Application Nos. 2017-100032 and 2018-021540, filed May 19, 2017 and Feb. 9, 2018, respectively, the disclosures of which are hereby incorporated by reference in their entirety.

TECHNICAL FIELD

The present invention relates to an active pharmaceutical ingredient carrier including an active pharmaceutical ingredient (API) carried by the silica, and a production method of the same.

BACKGROUND

Some pharmaceuticals are poorly water-soluble, and there is a problem of improving the solubility of poorly water-soluble drugs to effectively exhibit the desired drug efficacy. As a method of improving the solubility of poorly water-soluble drugs, there have been proposed, for example, a method of making a crystal form to highly soluble, and a method of improving the solubility by making a pharmaceutical carried by a porous inorganic material (see Patent Literatures 1 and 2).

For example, in Patent Literature 1, a tablet including composite particles in which silica and a poorly water-soluble drug having a solubility of 1 mg/ml or less are combined is proposed.

In Patent Literature 2, use of an inorganic particle-like material mainly composed of silicon oxide and including a mesopore and a macropore as a carrier is proposed, and improvement of the elution rate of itraconazole carried by the inorganic particle-like material is shown.

RELATED ART DOCUMENTS

Patent Documents

Patent Document 1: JP 2006-248922 A
Patent Document 2: JP 2014-522363 A

However, we performed a solubility test of a drug under conditions similar to biological environment using the above-mentioned tablet, or the above-mentioned carrier as a drug carrier and proved that the solubility is improved but not sufficient so further improvement is required. It was also proved that the solubility is decreased the lapse of time even though the solubility of the drug is improved just after the addition of the carrier into an aqueous medium such as biological environment, thus the improvement is required also from the viewpoint of sustainability of the drug efficacy. Further, from the view of the production costs of the carrier, the production conditions of the inorganic particle-like material including a mesopore and a macropore described in Patent Literature 2 are complicated and expensive, so there is a room for improvement.

SUMMARY OF THE INVENTION

Thus, one embodiment of the present invention is to provide an active pharmaceutical ingredient carrier having excellent solubility and sustained release of an active pharmaceutical ingredient.

As a result of intensive studies in view of the above problems, the present inventors have found that the above problems can be solved according to the following configuration examples, thereby completing the present invention.

That is, the active pharmaceutical ingredient carrier (a drug carrier) according to one embodiment of the present invention is an active pharmaceutical ingredient carrier including silica having a volume of a pore with a pore radius of 1 to 100 nm determined by BJH method of 3.0 to 5.0 ml/g, and a peak of a pore radius of 10 to 50 nm determined by BJH method; and an active pharmaceutical ingredient carried by the silica.

The active pharmaceutical ingredient carrier according to one embodiment of the present invention can suitably adopt the following aspects.

1) A volume of a pore with a pore radius in a range of 10 to 50 nm in the silica occupies 60% or more of a total pore volume.
2) The silica is hydrophilic.
3) The active pharmaceutical ingredient carried by the active pharmaceutical ingredient carrier is amorphous.

One embodiment of the present invention is to provide a production method of the active pharmaceutical ingredient carrier, including the step of: dissolving an active pharmaceutical ingredient in an organic solvent, then adding silica, and removing the organic solvent, wherein the silica has a volume of a pore with a pore radius of 1 to 100 nm determined by BJH method of 3.0 to 5.0 ml/g, and a peak of a pore radius of 10 to 50 nm determined by BJH method.

Effect of the Invention

According to one embodiment of the present invention, by making the active pharmaceutical ingredient carried by silica having a specific pore volume and pore radius, not only does the solubility of an active pharmaceutical ingredient, in particular, a poorly water-soluble active pharmaceutical ingredient, dramatically improve, but also surprisingly, the solubility of the active pharmaceutical ingredient can be sustained at a constant rate for a long time (excellent sustained release).

Though the details of the reason why the active pharmaceutical ingredient carrier according to one embodiment of the present invention (hereinafter also referred to as "the present active pharmaceutical ingredient carrier") has the above-mentioned effects are not clear, the present inventors presume as follows.

That is, the silica used for the present active pharmaceutical ingredient carrier has a specific pore volume and pore radius, and it is presumed that the active pharmaceutical ingredient carried is contained in an amorphous state inside the pore diameter of the silica. In particular, it is presumed that when the active pharmaceutical ingredient carrier is produced by a production method according to one embodiment of the present invention (hereinafter also referred to as "the present production method"), the active pharmaceutical ingredient is present in an amorphous state and contained inside the pore diameter of the silica. Amorphous substances generally have higher solubility in water than crystalline substances, and thus, it is presumed that the solubility of the active pharmaceutical ingredient is dramatically improved when the active pharmaceutical ingredient carrier is added into an aqueous medium such as an ecological environment. Further, in this case, it is presumed that the solubility depending on the hydrophilicity of the silica is exhibited, and thus, it is presumed that the solubility of the active pharmaceutical ingredient in an aqueous medium is further improved by using hydrophilic silica as the silica.

It is presumed that when the present active pharmaceutical ingredient carrier is contacted with the aqueous medium, water as a solvent infiltrates into the silica and gradually contacts the active pharmaceutical ingredient inside the pore, and thus the solubility of the active pharmaceutical ingredient is sustained for a long time.

As described above, according to the present active pharmaceutical ingredient carrier, the solubility of an active pharmaceutical ingredient, in particular, a poorly water-soluble active pharmaceutical ingredient, in water is dramatically improved, and further the solubility is sustained for a long time, and thus the present active pharmaceutical ingredient carrier is useful as a carrier for various active pharmaceutical ingredients, in particular, poorly water-soluble active pharmaceutical ingredients.

DESCRIPTION OF THE INVENTION

Active Pharmaceutical Ingredient Carrier

The present active pharmaceutical ingredient carrier includes silica having a volume of a pore with a pore radius of 1 to 100 nm determined by BJH method of 3.0 to 5.0 ml/g, and a peak of a pore radius of 10 to 50 nm determined by BJH method; and an active pharmaceutical ingredient carried by the silica. According to such an active pharmaceutical ingredient carrier, not only does the solubility of an active pharmaceutical ingredient, in particular, a poorly water-soluble active pharmaceutical ingredient, dramatically improve, but also surprisingly, the solubility of the active pharmaceutical ingredient can be sustained at a constant rate for a long time.

Figure 1:
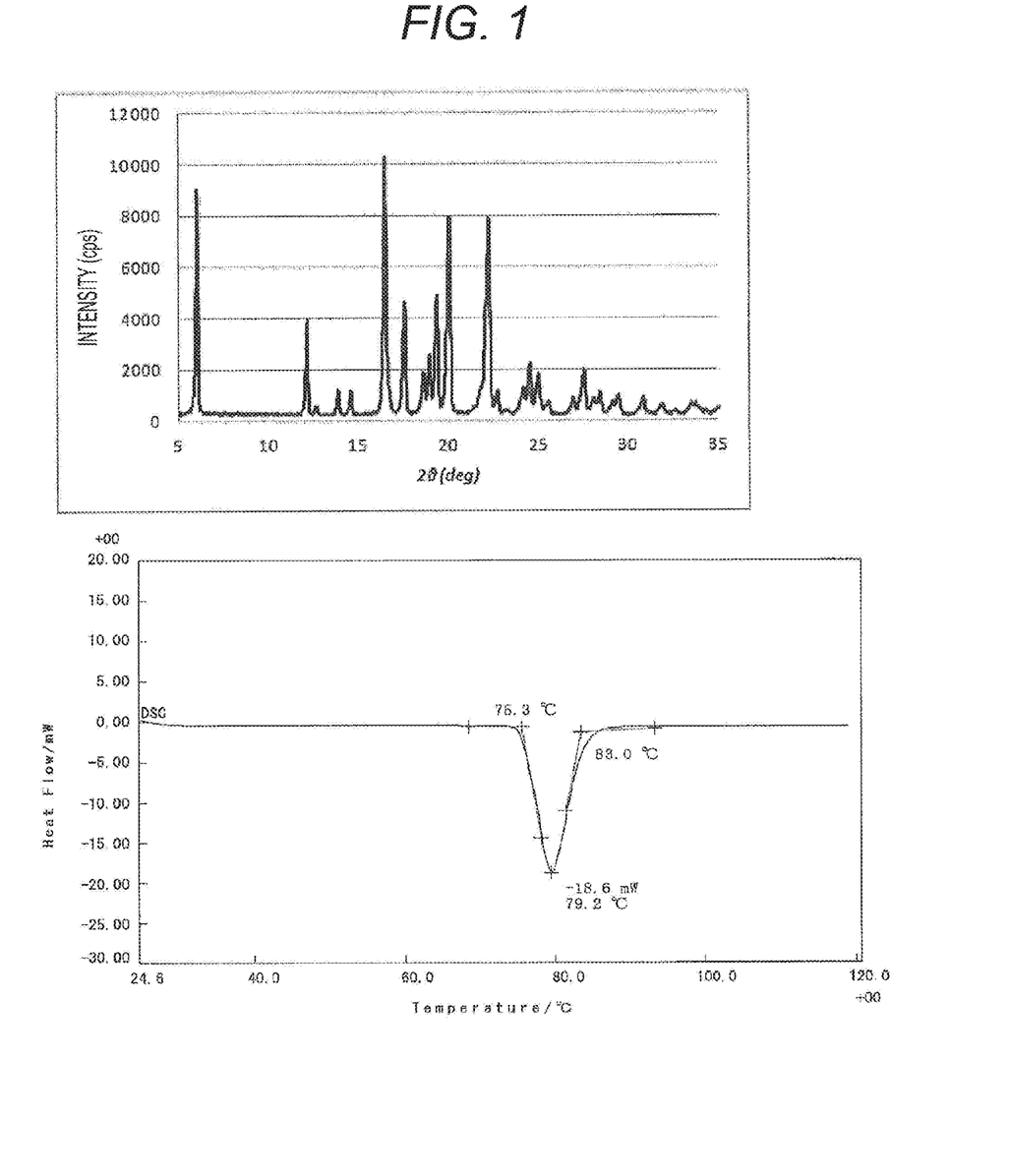
FIG. 1 shows an X-ray crystal diffraction peak (upper figure) and a DSC chart (lower figure) of ibuprofen.
Figure 2:
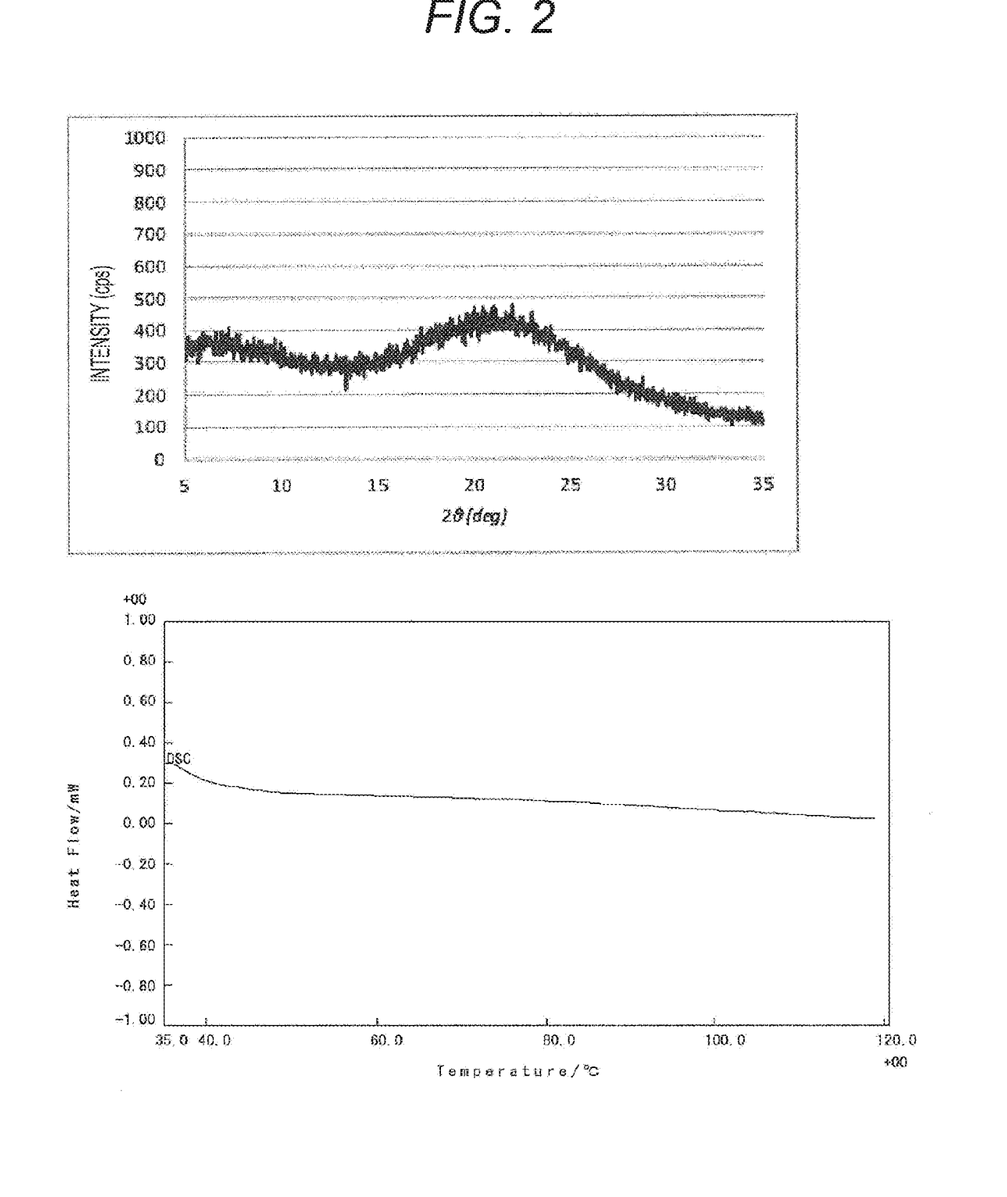
FIG. 2 shows an X-ray crystal diffraction peak (upper figure) and a DSC chart (lower figure) of the present active pharmaceutical ingredient carrier including ibuprofen carried.

FIG. 2 shows an X-ray crystal diffraction peak and a DSC chart of the present active pharmaceutical ingredient carrier including an antipyretic analgesic antiinflammatory agent, ibuprofen (IBP), carried. As is obvious from the comparison to the X-ray crystal diffraction peak and the DSC chart of the IBP crystal in FIG. 1, no diffraction peak characteristic of the IBP crystal is detected in the X-ray crystal diffraction peak for the present active pharmaceutical ingredient carrier. From this, it is presumed that in the present active pharmaceutical ingredient carrier, IBP, the active pharmaceutical ingredient, is not carried on the silica surface, but is contained inside the pore diameter of silica. As is obvious from the comparison to the DSC charts, the endothermic peak observed in the IBP crystal is not detected in the present active pharmaceutical ingredient carrier, and thus it is presumed that the IBP in the present active pharmaceutical ingredient carrier is present in an amorphous state.

Figure 3:
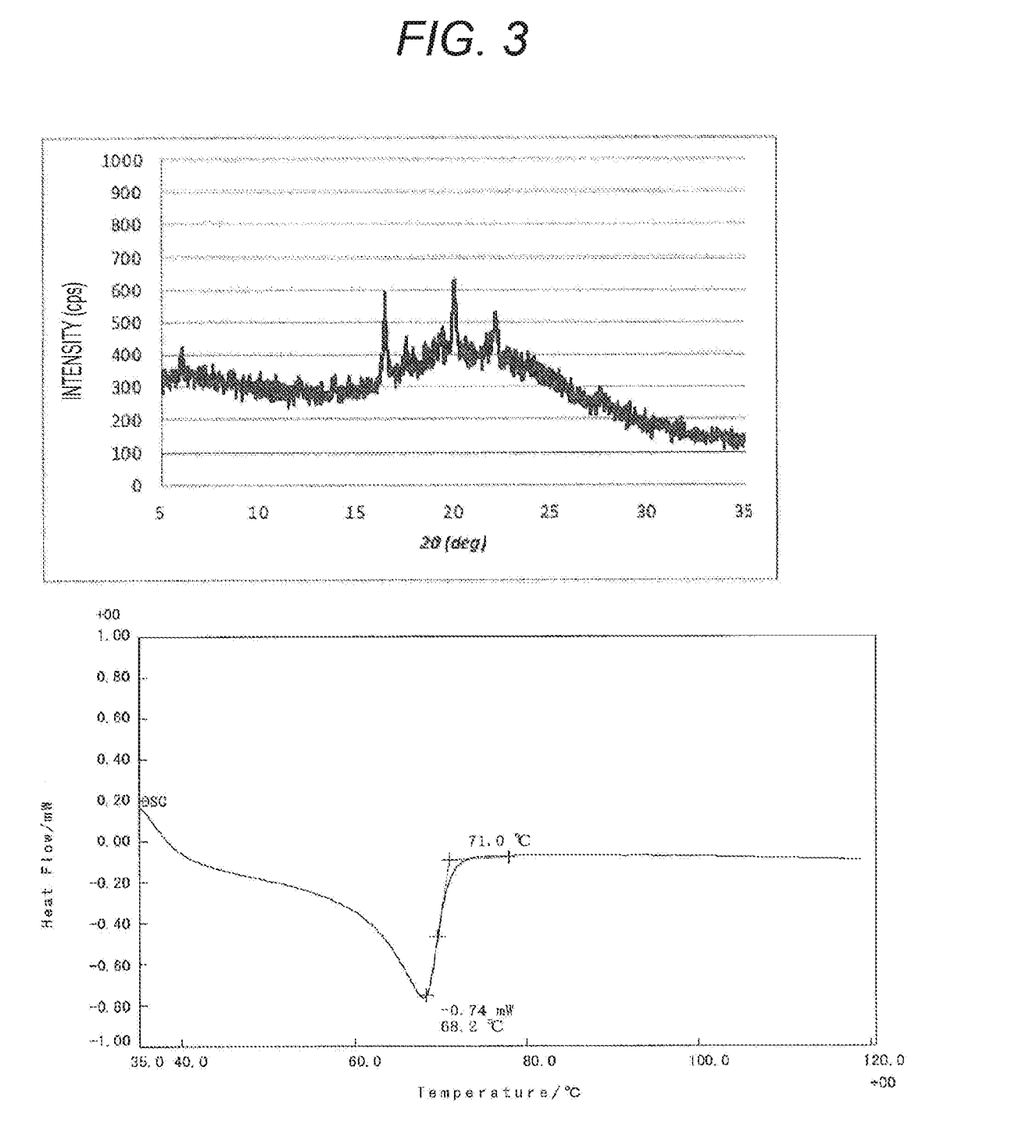
FIG. 3 shows an X-ray crystal diffraction peak (upper figure) and a DSC chart (lower figure) of a carrier including silica B and ibuprofen carried by the silica B.

Meanwhile, FIG. 3 shows an X-ray crystal diffraction peak and a DSC chart of an active pharmaceutical ingredient carrier including silica B having a volume of a pore with a pore radius of 1 to 100 nm of 1.1 ml/g and a peak value of a pore radius of 13 nm and IBP carried by the silica B. In FIG. 3, the X-ray crystal diffraction peak and the endothermic peak in the DSC chart similar to that of the IBP crystal are present, and thus it is presumed that the IBP carried by the silica B is carried on the silica surface in a crystal state.

Figure 4:
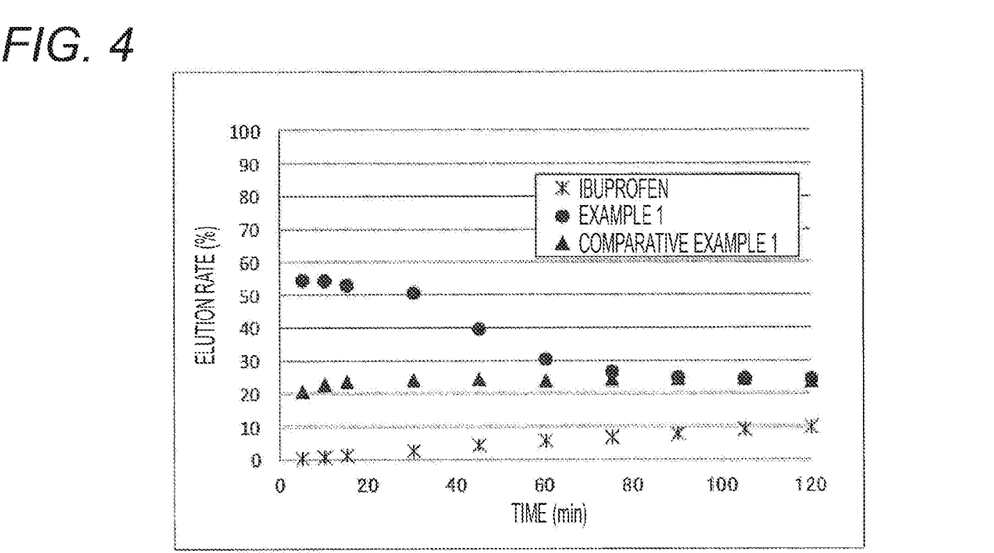
FIG. 4 shows the result of the elution test in the elution test solution No. 1 (pH 1.2) of the present active pharmaceutical ingredient carrier including ibuprofen carried, a carrier including silica B and ibuprofen carried by the silica B, and an ibuprofen crystal (ibuprofen).

FIG. 4 shows the result of the elution test in the elution test solution No. 1 of the active pharmaceutical ingredient and the active pharmaceutical ingredient carrier. The elution test solution No. 1 is an aqueous solution with pH 1.2 and reproduces the state in gastric juice. In the figure, the vertical axis represents the elution rate of IBP, and the horizontal axis represents the elapsed time when the time of addition of the active pharmaceutical ingredient or active pharmaceutical ingredient carrier to the aqueous solution is 0 minute.

The elution test was performed according to the paddle method in the Japanese Pharmacopoeia the 17th edition. Specifically, the test solution was set to 900 mL of the elution test solution No. 1 of the Japanese Pharmacopoeia, the temperature was set to 37±0.5° C., the rotation speed was set to 75 rpm, the sample to be tested was loaded, and then about 1 mL was sampled at regular intervals, filtered through a syringe filter, and then subjected to HPLC analysis to determine the peak area of the active pharmaceutical ingredient. The obtained area was compared to the peak area of the active pharmaceutical ingredient at the elution rate of 100% to calculate the elution rate (%).

The elution rate is a value obtained by performing HPLC analysis with 200 mg of an IBP crystal all dissolved in 900 mL of the test solution, taking the obtained area as the elution rate of 100%, adding the active pharmaceutical ingredient or the active pharmaceutical ingredient carrier to the eluate, then performing sampling overtime, performing filtering and HPLC analysis to calculate the area, and comparing the area to the value of the elution rate of 100%.

As is obvious from the result of FIG. 4, it was found that the present active pharmaceutical ingredient carrier has dramatically improved solubility compared to an IBP crystal and the solubility of the active pharmaceutical ingredient is sustained for a long time. Meanwhile, though the carrier including silica B and IBP carried by the silica B has an effect of improving the solubility of the active pharmaceutical ingredient compared to an IBP crystal, the solubility of the active pharmaceutical ingredient is low compared to the present active pharmaceutical ingredient carrier, and thus it is found that the present active pharmaceutical ingredient carrier has a high effect of improving the solubility of the active pharmaceutical ingredient.

As described above, the details of the reason why the present active pharmaceutical ingredient carrier exhibits high solubility and sustained release in the elution test solution compared to the active pharmaceutical ingredient are unknown, the present inventors presume as follows.

That is, as is obvious from the X-ray crystal diffraction peak and the DSC chart, it is presumed that the active pharmaceutical ingredient in the present active pharmaceutical ingredient carrier is present in an amorphous state. In general, the active pharmaceutical ingredient alone is more soluble in an aqueous medium (for example, water and a body fluid or a body fluid-like liquid such as the above-mentioned aqueous solution) in an amorphous state than in a crystal state, and thus it is presumed that the present active pharmaceutical ingredient carrier also exhibits high solubility of the active pharmaceutical ingredient. The carrier in the present active pharmaceutical ingredient carrier is silica having a specific pore volume and pore radius, and it is presumed that the active pharmaceutical ingredient is contained inside the pore inside the silica, and the active pharmaceutical ingredient is gradually dissolved due to the contact with the aqueous medium. It is presumed that due to such an effect, the present active pharmaceutical ingredient carrier exhibits highly sustained release.

Silica

The silica has a volume of a pore with a pore radius of 1 to 100 nm determined by BJH method of 3.0 to 5.0 ml/g, and a peak of a pore radius of 10 to 50 nm determined by BJH method. By using silica having such a specific pore volume and pore radius, the above-described effect is exhibited.

In the present invention, "volume of a pore with a pore radius of 1 to 100 nm determined by BJH method" means the volume of a pore with a pore radius of 1 nm to 100 nm obtained by drying the sample to be measured at a temperature of 200° C. for 3 hours or more under a vacuum of 1 kPa or less, then measuring the adsorption isotherm of only the nitrogen adsorption side at liquid nitrogen temperature, and analyzing the adsorption isotherm by the BJH method.

"Peak of a pore radius determined by BJH method" means the value of the pore radius having the maximum peak value in the pore distribution curve (volume distribution curve) obtained by analyzing the adsorption isotherm of the adsorption side obtained in the same manner as described above by BJH method and plotting the cumulative pore volume differentiated by the logarithm of the pore radius on the vertical axis and the pore radius on the horizontal axis.

For example, from the viewpoint of increasing the carried amount of the active pharmaceutical ingredient, and from the viewpoint of containing the active pharmaceutical ingredient in an amorphous state, the volume of a pore with a pore radius of 1 to 100 nm is preferably 3.0 to 4.0 ml/g. For example, from the viewpoint of maintaining the solubility improvement effect of the active pharmaceutical ingredient over time, the peak of the pore radius is preferably in the range of 10 to 40 nm, more preferably 10 to 30 nm.

For example, from the viewpoint of making the active pharmaceutical ingredient carried inside the pore, and from the viewpoint of the sustained release of the active pharmaceutical ingredient when the present active pharmaceutical ingredient carrier is contacted with an aqueous medium, a volume of a pore with a pore radius in a range of 10 to 50 nm in the silica preferably occupies 60% or more, more preferably 70% or more, and particularly preferably 75% or more of the total pore volume, 100%.

Specifically, the ratio of the volume of a pore with a pore radius in the range of 10 to 50 nm can be measured by the method described in Examples below.

The particle size of the silica can be appropriately determined in consideration of the shape of the drug containing the present active pharmaceutical ingredient carrier (for example, a tablet, a granule, and a capsule) and the like, however, for example, from the viewpoint of efficiently exhibiting the drug efficacy and from the viewpoint of excellent dispersibility of the active pharmaceutical ingredient carrier in an aqueous medium, the $D_{50}$ value based on the volume in the particle size distribution measurement by the Coulter counter method or the laser diffraction method is preferably 1 to 100 μm, more preferably 1 to 50 μm.

The bulk density of the silica is preferably in a range of 20 to 200 g/L, more preferably 50 to 120 g/L, and the oil absorption is preferably 400 to 600 ml/100 g, more preferably 450 to 600 ml/100 g, for example, from the viewpoint of handling properties for use in drugs, and from the viewpoint of affinity with other components (for example, solvents) used in the formation of drugs.

Specifically, the bulk density and the oil absorption can be measured by the methods described in Examples below.

The silica is preferably hydrophilic, for example, from the viewpoint of dispersibility of the active pharmaceutical ingredient carrier in an aqueous medium and from the viewpoint of the solubility of the active pharmaceutical ingredient.

Whether the silica is hydrophilic or not can be determined by the dispersibility when the silica is contacted with water. The hydrophilic silica is dispersed in water, but the hydrophobic silica floats on the water. Whether the silica is hydrophilic or not can also be determined by the M value.

Examples of the silica include silica aerogel. The silica aerogel can be usually obtained by producing silica hydrogel by hydrolysis of alkali metal silicate or alkoxysilane and then drying the silica hydrogel by a method such as supercritical drying.

Examples of the production method of silica having the above-mentioned physical properties include the method described in WO 2012/057086. Specifically, the production method of aerogel including the following steps in this order is preferable:

(1) preparing aqueous silica sol, (2) dispersing the aqueous silica sol in a hydrophobic solvent to form a W/O emulsion, (3) gelling the silica sol to convert the W/O emulsion into a dispersion of gel, (4) replacing the water in the gel with a solvent having a surface tension at 20° C. of 30 mN/m or less, (5) treating the gel with a hydrophobizing agent, and (6) removing the solvent used for replacing.

The silica obtained by these methods is hydrophobic. However, when the silica is held at 500 to 700° C. for about 3 hours in an air atmosphere using an electric furnace, the hydrophobic group on the surface burns, and the silica can be made hydrophilic.

Active Pharmaceutical Ingredient

The active pharmaceutical ingredient used in the present active pharmaceutical ingredient carrier is not particularly limited, and known active pharmaceutical ingredients can be used according to the desired use.

According to the above-mentioned presumption, such an active pharmaceutical ingredient is preferably an active pharmaceutical ingredient that can be carried in the pore of silica, and in particular, an organic active pharmaceutical ingredient having a relatively low molecular weight of about 100 to 1,000 is suitably used in terms of the above-mentioned effect.

Because the present active pharmaceutical ingredient carrier can improve the solubility of the active pharmaceutical ingredient in an aqueous medium, for example, from the viewpoint of better demonstration of the effect of the present invention, the active pharmaceutical ingredient is preferably a poorly water-soluble active pharmaceutical ingredient, and in particular, a poorly water-soluble active pharmaceutical ingredient having a solubility at 25° C. in water of 1 mg/ml or less is preferably used. Examples of such an active pharmaceutical ingredient include ibuprofen, acetaminophen, azilsartan, probucol, ezetimibe, celecoxib, itraconazole, mosapride citrate, nifedipine, ketoconazole, and naphthopidyl.

It is thought that, in particular, an active pharmaceutical ingredient having a hydroxyl group can be strongly fixed by a chemical action (for example, hydrogen bonding) with a hydroxyl group in the pore of silica, the carrier, and increase the sustained release properties of the active pharmaceutical ingredient. Thus, such an active pharmaceutical ingredient is suitable as the active pharmaceutical ingredient when the present active pharmaceutical ingredient carrier having excellent sustained release is required.

Meanwhile, because the present active pharmaceutical ingredient carrier can maintain the solubility of the active pharmaceutical ingredient at a constant rate for a long time, when the active pharmaceutical ingredient having high solubility in water is carried by the present active pharmaceutical ingredient carrier, the solubility of the active pharmaceutical ingredient can be maintained at a constant rate for a long time.

The state of the active pharmaceutical ingredient carried by the active pharmaceutical ingredient carrier is not particularly limited, it is preferably in an amorphous state, for example, from the viewpoint of obtaining the active pharmaceutical ingredient carrier excellent in the solubility of the active pharmaceutical ingredient.

The amount of the active pharmaceutical ingredient carried by silica is preferably in a range that allows the active pharmaceutical ingredient to be carried in an amorphous state and further to be maintained in an amorphous state for a long time in the carrier, and the amount of the active pharmaceutical ingredient carried is 10 to 80% by weight, further preferably 20 to 50% by weight relative to the total amount of the carrier.

Production Method of Active Pharmaceutical Ingredient Carrier

The production method is not particularly limited as long as the active pharmaceutical ingredient is carried by silica, and known methods can be used. Specifically, examples of the method include (I) a method including the step of adding an active pharmaceutical ingredient and silica to a solvent to make the active pharmaceutical ingredient carried by the silica, then separating them by filtration and the like, and removing the solvent, for example, by drying the solvent and the like, (II) a method including the step of dissolving an active pharmaceutical ingredient in an organic solvent and the like, then adding silica to make the active pharmaceutical ingredient carried by the silica, then separating them by filtration and the like, and removing the organic solvent and the like, for example, by drying the organic solvent and the like, and (III) a method including the step of dropping a solution obtained by dissolving an active pharmaceutical ingredient in an organic solvent and the like into a dispersion in which silica is previously dispersed, and removing the organic solvent and the like, for example, by drying the organic solvent and the like.

To make the active pharmaceutical ingredient carried by the silica, dispersing can be performed using ultrasound.

In particular, in the method (II), the active pharmaceutical ingredient can be carried by silica in an amorphous state, and thus the method (II) is most suitable from the viewpoint of improving the solubility of the active pharmaceutical ingredient in an aqueous medium.

The organic solvent and the like are not particularly limited as long as the active pharmaceutical ingredient can be dissolved in them. Examples of the organic solvent include acetone.

The amount of the organic solvent and the like used is not particularly limited as long as it is an amount sufficient to allow the active pharmaceutical ingredient to be dissolved, and the amount is usually in a range of 10 to 200 parts by mass of the organic solvent and the like per 1 part by mass of the active pharmaceutical ingredient.

The active pharmaceutical ingredient is dissolved in an organic solvent or the like, and then silica is added. The temperature to make the active pharmaceutical ingredient carried by the silica is not particularly limited. The temperature can be usually appropriately set in the range of 20 to 60° C. The time to make the active pharmaceutical ingredient carried by the silica is also not particularly limited, and about 1 minute to 1 hour is usually enough.

Further, for example, from the viewpoint of efficiently making the active pharmaceutical ingredient carried by silica, the active pharmaceutical ingredient can be carried by silica while performing dispersing with ultrasound or stirring with a stirrer. The obtained active pharmaceutical ingredient carrier can be used as it is for tableting by a wet process without being dried, or the obtained active pharmaceutical ingredient carrier can be used for a desired purpose after being dried.

The method of drying after the active pharmaceutical ingredient is carried by silica can be any method by which the organic solvent and the like can be removed, and examples thereof include vacuum concentration with an evaporator and vacuum drying under heating conditions. The dried active pharmaceutical ingredient carrier can be used as it is, or can be grinded or crushed as needed.

Aspect of Using Active Pharmaceutical Ingredient Carrier

The present active pharmaceutical ingredient carrier can be used as it is, or it can also be used as a tablet by incorporating an excipient and the like. It can also be used as a patch or inhalant.

The present active pharmaceutical ingredient carrier usually releases the active pharmaceutical ingredient carried therein when the present active pharmaceutical ingredient carrier is in contact with an aqueous medium, in particular, body fluid. Thus, the following elution test solution No. 1 and No. 2 were used as the active pharmaceutical ingredient release from the present active pharmaceutical ingredient carrier.

EXAMPLES

Hereinafter, the present invention will be described in detail with reference to Examples, but the present invention is not limited thereto.

In the Examples and Comparative Examples, hydrophilic silicas A to C shown in Table 1 below were used.

Silica A was synthesized based on the method described in WO 2012/057086, and Silica B was synthesized based on a conventionally known dry process. Silica C was a commercial product.

The measuring method of each physical property value of these silicas is as follows.

TABLE 1

|  | Silica A | Silica B | Silica C |
|---|---|---|---|
| Particle size $D_{50}$ (μm) | 8.6 | 7 | 5.2 |
| Specific surface area (m$^2$/g) | 618 | 362 | 609 |
| Pore volume (ml/g) | 3.5 | 1.1 | 1.8 |
| Peak value of pore radius (nm) | 19 | 13 | 17 |
| Ratio of the pore radius of 10 to 50 nm (%) | 80 | 65 | 32 |
| Oil absorption (ml/100 g) | 566 | 150 | 273 |
| Bulk density (g/l) | 109 | 50 | 220 |

Particle size (volume-based particle size $D_{50}$)

A product obtained by mixing 40 ml of ethanol and 0.01 g of silica and dispersing the mixture for 3 minutes with ultrasonic washing machine B1510J-MT manufactured by Emerson Japan, Ltd. was subjected to the measurement of particle size distribution with Multisizer III manufactured by Beckman Coulter, Inc. and an aperture tube 50 μm. The $D_{50}$ (μm) value in the obtained volume-based particle size distribution was determined.

Specific Surface Area

The sample to be measured was dried for 3 hours or more at a temperature of 200° C. under a vacuum of 1 kPa or less, then the adsorption isotherm of only the nitrogen adsorption side at the liquid nitrogen temperature was measured, and the adsorption isotherm was analyzed by BET method. The pressure range used for the analysis was a relative pressure of 0.1 to 0.25.

Pore Volume and Peak Value of Pore Radius

The pore volume (ml/g) in FIG. 1 above is the volume derived from the pore with a pore radius of 1 nm to 100 nm obtained by analyzing the adsorption isotherm of the adsorption side by BJH method (Barrett, E. P.; Joyner, L. G.; Halenda, P. P., J. Am. Chem. Soc. 73, 373 (1951)) obtained on the measurement of the specific surface area.

The peak value (nm) of the pore radius is the value of the pore radius having the maximum peak value in the pore distribution curve (volume distribution curve) obtained by analyzing the adsorption isotherm by BJH method and plotting the cumulative pore volume differentiated by the logarithm of the pore radius on the vertical axis and the pore radius on the horizontal axis.

The ratio (%) of the pore radius of 10 to 50 nm in Table 1 was calculated based on the following formula. In the following formula, the volume of a pore with a pore radius in the range of 10 to 50 nm and the volume of all pores of silica were measured in the same method as in the above-mentioned volume of a pore (with a pore radius of 1 to 100 nm).

Ratio of pore radius of 10 to 50 nm (%)=volume of pore with pore radius in the range of 10 to 50 nm×100/volume of all pores of silica Oil Absorption The oil absorption was measured by a method according to JIS K 5600-13-1. Specifically, 0.4 g of the sample to be measured is spread on a glass plate and mixed with oleic acid while dropping oleic acid. The end point is when the paste became smooth. The paste is capable of being spread without cracking or becoming rags and loosely adheres to the glass plate. The volume of the dropped oleic acid per 100 g of silica was taken as the oil absorption (ml/100 g).

Bulk Density

The bulk density was measured according to the bulk density measuring method No. 1 described in the Japanese Pharmacopoeia. In order to crush silica aggregates, the silica to be measured was passed through a sieve having an aperture of 2 mm before the measurement. About 5 g of silica passed through the sieve (the amount of silica used (g) was taken as Mg) was gently put into a dry 100 mL measuring cylinder without compaction. The surface of the powder layer was carefully leveled without compaction as needed, and the aerated bulk volume (V) was read with the minimum scale unit. Bulk density (g/l) was calculated by M/V.

Example 1

To a 200 mL eggplant flask, 1.0 g of ibuprofen and 50 mL of acetone were added and dissolved uniformly at room temperature. Subsequently, 2.3 g of hydrophilic silica A was added thereto and the mixture was shaken at room temperature to be uniformly dispersed. The obtained dispersion was concentrated with a rotary evaporator at 40° C. to obtain a wet active pharmaceutical ingredient carrier. The wet active pharmaceutical ingredient carrier was vacuum dried at 50° C. to obtain an active pharmaceutical ingredient carrier with a recovery rate of 92%.

Example 2

An active pharmaceutical ingredient carrier was obtained with a recovery rate of 85% in the same operation as in Example 1 except that an eggplant flask was immersed in an ultrasonic bath to disperse the mixture by insonation at 20 to 50° C. for 20 minutes, instead of shaking in Example 1.

Example 3

To a 200 mL three-necked flask equipped with an overhead stirrer, 2.3 g of hydrophilic silica A was added and heated to 60° C. An ibuprofen solution in which 1.0 g of ibuprofen was dissolved in 50 mL of acetone was prepared, put into a 100 mL dropping funnel, and dropped while evaporating acetone with nitrogen gas with stirring, thereby a wet active pharmaceutical ingredient carrier was obtained. The obtained wet active pharmaceutical ingredient carrier was vacuum dried at 50° C. to obtain an active pharmaceutical ingredient carrier with a recovery rate of 87%.

Comparative Examples 1 and 2

An active pharmaceutical ingredient carrier was prepared in the same operation as in Example 1 except that hydrophilic silica B (Comparative Example 1) or hydrophilic silica C (Comparative Example 2) was used instead of hydrophilic silica A. The recovery rate was 93% for Comparative Example 1 and 88% for Comparative Example 2.

Elution Test

An active pharmaceutical ingredient carrier (corresponding to 200 mg of an active pharmaceutical ingredient) (0.66 g) was weighed, and subjected to the elution test according to the paddle method in the Japanese Pharmacopoeia elution test method using the elution test solution No. 1 (pH 1.2). The temperature of the test solution was 37±0.5° C., and the rotation speed was 75 rpm. Sampling was performed at 5 minutes, 10 minutes, 15 minutes, 30 minutes, and then once every 15 minutes until 120 minutes after addition of the active pharmaceutical ingredient carrier, the obtained sample was immediately filtered using a syringe filter, and the elution rate (%) was calculated as described above from the peak area of the active pharmaceutical ingredient by high performance liquid chromatography (HPLC) with a UV detector.

The elution test of an IBP crystal was performed in the same manner as described above except that an ibuprofen active pharmaceutical ingredient (IBP crystals) was used instead of the active pharmaceutical ingredient carrier.

The results are shown in Table 2. The results of the elution test when the active pharmaceutical ingredient carrier obtained in Example 1 or Comparative Example 1, or an IBP crystal (ibuprofen) was used are shown in FIG. 4.

TABLE 2

|  | Elution rate (%) | | |
| --- | --- | --- | --- |
|  | 10 min | 60 min | 120 min |
| Example 1 | 54.3 | 31.0 | 24.3 |
| Example 2 | 54.6 | 30.7 | 24.7 |
| Example 3 | 54.1 | 30.5 | 23.9 |
| Comparative Example 1 | 23.0 | 24.1 | 24.0 |
| Comparative Example 2 | 32.4 | 23.6 | 23.9 |
| IBP crystal | 1.1 | 6.0 | 10.1 |

As is obvious from the results, it was found that the present active pharmaceutical ingredient carrier has dramatically improved solubility compared to an IBP crystal and the solubility is sustained for a long time. Meanwhile, though the carrier including silica B or C and IBP carried by the silica B or C has an effect of improving the solubility compared to an IBP crystal, the solubility of the active pharmaceutical ingredient is low compared to the present active pharmaceutical ingredient carrier, and thus it is found that the present active pharmaceutical ingredient carrier has a high effect of improving the solubility of the active pharmaceutical ingredient even compared to the carrier including silica B or C and IBP carried by the silica B or C.

X-Ray Crystal Diffraction Peak

The X-ray crystal diffraction peak of an IBP crystal or the active pharmaceutical ingredient carrier obtained in Example 1 or Comparative Example 1 was measured under conditions of tube voltage-current: 40 kV-30 mA, and a measurement angle: 5 to 35 deg using X-ray diffraction analyzer SmartLab manufactured by Rigaku Corporation.

The peak of an IBP crystal is shown in the upper figure in FIG. 1, the peak of the active pharmaceutical ingredient carrier obtained in Example 1 is shown in the upper figure in FIG. 2, and the peak of the active pharmaceutical ingredient carrier obtained in Comparative Example 1 is shown in the upper figure in FIG. 3.

DSC Chart

The DSC chart of an IBP crystal or the active pharmaceutical ingredient carrier obtained in Example 1 or Comparative Example 1 was measured at a heating rate of 10° C./min using differential scanning calorimeter DSC8230 manufactured by Rigaku Corporation.

The DSC chart of an IBP crystal is shown in the lower figure in FIG. 1, the DSC chart of the active pharmaceutical ingredient carrier obtained in Example 1 is shown in the lower figure in FIG. 2, and the DSC chart of the active pharmaceutical ingredient carrier obtained in Comparative Example 1 is shown in the lower figure of FIG. 3.

Example 4

To a 200 mL eggplant flask, 1.0 g of ezetimibe (ETB) and 50 mL of acetone were added and dissolved uniformly at room temperature. Subsequently, 2.3 g of hydrophilic silica A was added. The eggplant flask was immersed in an ultrasound bath to disperse the mixture by ultrasound at 20 to 50° C. for 20 minutes. The obtained dispersion was concentrated with a rotary evaporator at 40° C. to obtain a wet active pharmaceutical ingredient carrier. The wet active pharmaceutical ingredient carrier was vacuum dried at 50° C. to obtain an active pharmaceutical ingredient carrier with a recovery rate of 97%.

In the same manner as described above, X-ray crystal diffraction measurement and DSC measurement of the obtained active pharmaceutical ingredient carrier were performed to confirm that the ETB carried by the active pharmaceutical ingredient carrier is amorphous, and the ETB is carried in pores.

Elution Test

In the same manner as in the elution test, the elution test of the obtained active pharmaceutical ingredient carrier or the ezetimibe active ingredient (an ETB crystal) was performed. This test was performed using the elution test solution No. 1 (pH 1.2) same as that described above and the elution test solution No. 2 (pH 6.8).

Figure 5:
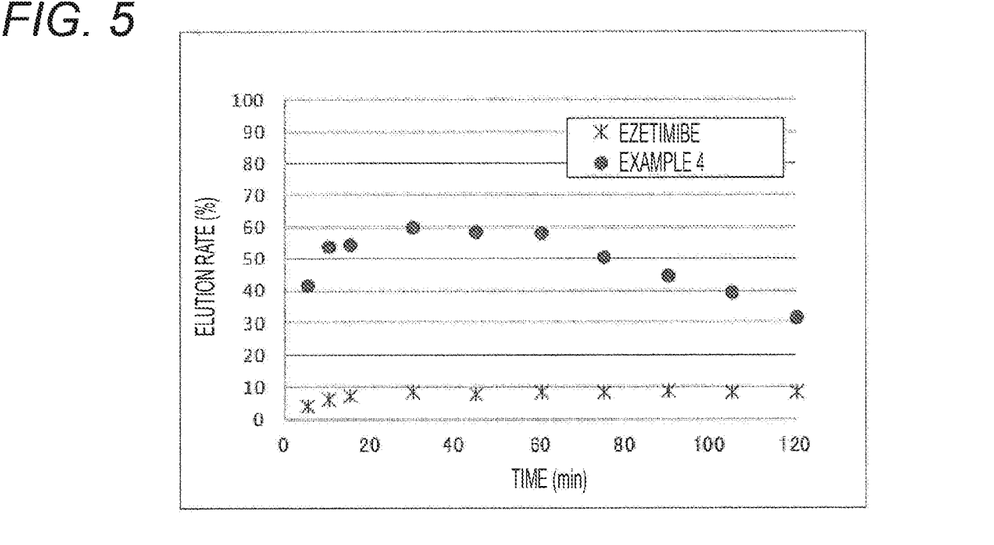
FIG. 5 shows the result of the elution test in the elution test solution No. 1 (pH 1.2) of the present active pharmaceutical ingredient carrier including ezetimibe carried and an ezetimibe crystal (ezetimibe).
Figure 6:
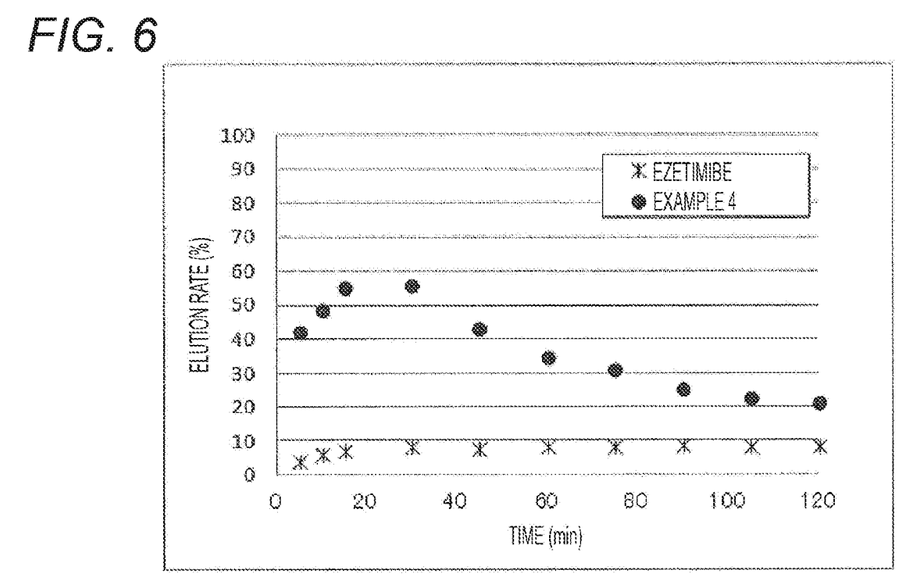
FIG. 6 shows the result of the elution test in the elution test solution No. 2 (pH 6.8) of the present active pharmaceutical ingredient carrier including ezetimibe carried and ezetimibe.

The results are shown in Table 3. The results of the elution test when the elution test solution No. 1 was used are shown in FIG. 5, and the results of the elution test when the elution test solution No. 2 was used are shown in FIG. 6.

TABLE 3

|  |  | Elution rate (%) | | |
| --- | --- | --- | --- | --- |
|  |  | 10 min | 60 min | 120 min |
| Example 4 | Elution test solution No. 1 (pH 1.2) | 53.8 | 58.1 | 31.5 |
| ETB crystal | | 6.1 | 8.4 | 8.4 |
| Example 4 | Elution test solution No. 2 (pH 6.8) | 48.5 | 34.6 | 21.2 |
| ETB crystal | | 6.6 | 8.3 | 8.2 |

Example 5

To a 200 mL eggplant flask, 1.0 g of celecoxib (CXB) and 50 mL of acetone were added and dissolved uniformly at room temperature. Subsequently, 2.3 g of hydrophilic silica A was added. The eggplant flask was immersed in an ultrasound bath to disperse the mixture by ultrasound at 20 to 50° C. for 20 minutes. The obtained dispersion was concentrated with a rotary evaporator at 40° C. to obtain a wet active pharmaceutical ingredient carrier. The wet active pharmaceutical ingredient carrier was vacuum dried at 50° C. to obtain an active pharmaceutical ingredient carrier with a recovery rate of 88%.

In the same manner as described above, X-ray crystal diffraction measurement and DSC measurement of the obtained active pharmaceutical ingredient carrier were performed to confirm that the CXB carried by the active pharmaceutical ingredient carrier is amorphous, and the CXB is carried in pores.

Elution Test

In the same manner as described above, the elution test of the obtained active pharmaceutical ingredient carrier or the celecoxib active ingredient (a CXB crystal) was performed using the elution test solution No. 1 (pH 1.2) or the elution test solution No. 2 (pH 6.8).

Figure 7:
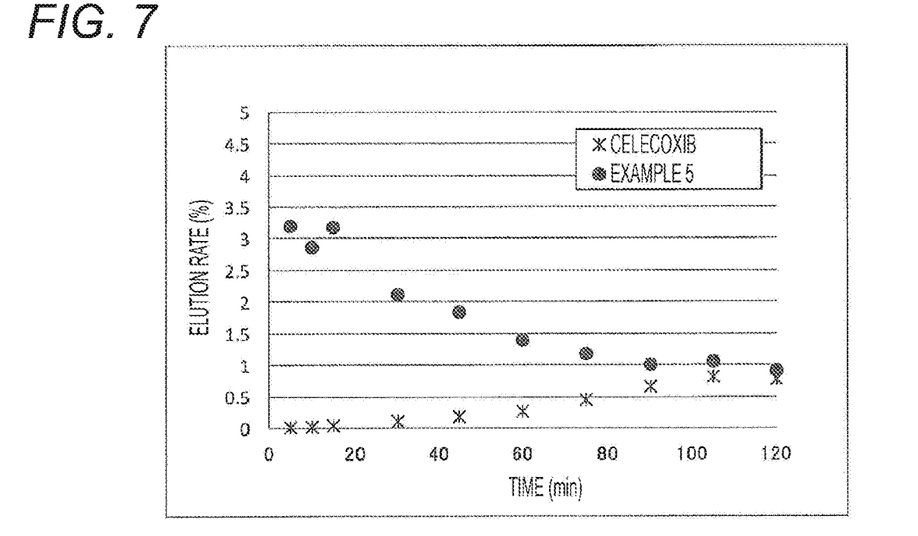
FIG. 7 shows the result of the elution test in the elution test solution No. 1 (pH 1.2) of the present active pharmaceutical ingredient carrier including celecoxib carried and a celecoxib crystal (celecoxib).
Figure 8:
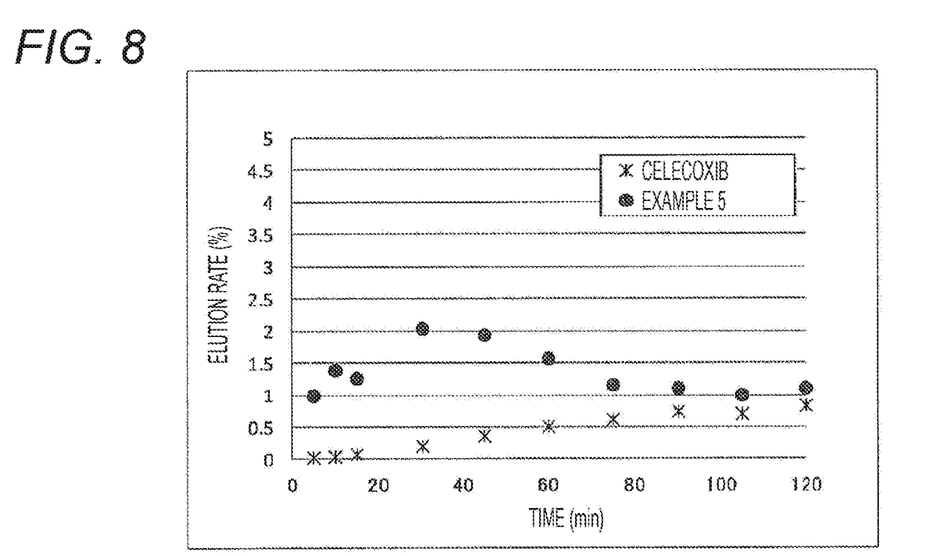
FIG. 8 shows the result of the elution test in the elution test solution No. 2 (pH 6.8) of the present active pharmaceutical ingredient carrier including celecoxib carried and celecoxib.

The results are shown in Table 4. The results of the elution test when the elution test solution No. 1 was used are shown in FIG. 7, and the results of the elution test when the elution test solution No. 2 was used are shown in FIG. 8.

TABLE 4

| | | Elution rate (%) | | |
|---|---|---|---|---|
| | | 10 min | 60 min | 120 min |
| Example 5 | Elution test | 2.9 | 1.4 | 0.93 |
| CXB crystal | solution No. 1 (pH 1.2) | 0.035 | 0.28 | 0.79 |
| Example 5 | Elution test | 1.4 | 1.6 | 1.1 |
| cxB crystal | solution No. 2 (pH 6.8) | 0.042 | 0.51 | 0.84 |

Example 6

To a 200 mL eggplant flask, 1.0 g of azilsartan (AZL), 40 mL of acetone, and 10 mL of dimethyl sulfoxide were added and uniformly dissolved at room temperature. Subsequently, 2.3 g of hydrophilic silica A was added. The eggplant flask was immersed in an ultrasound bath to disperse the mixture by ultrasound at 20 to 50° C. for 20 minutes. The dispersion was concentrated with a rotary evaporator at 40° C. to obtain a wet active pharmaceutical ingredient carrier. The wet active pharmaceutical ingredient carrier was vacuum dried at 60° C. to obtain an active pharmaceutical ingredient carrier with a recovery rate of 98%.

In the same manner as described above, X-ray crystal diffraction measurement and DSC measurement of the obtained active pharmaceutical ingredient carrier were performed to confirm that the AZL carried by the active pharmaceutical ingredient carrier is amorphous, and the AZL is carried in pores.

Elution Test

In the same manner as described above, the elution test of the obtained active pharmaceutical ingredient carrier or the azilsartan active ingredient (an AZL crystal) was performed using the elution test solution No. 1 (pH 1.2).

Figure 9:
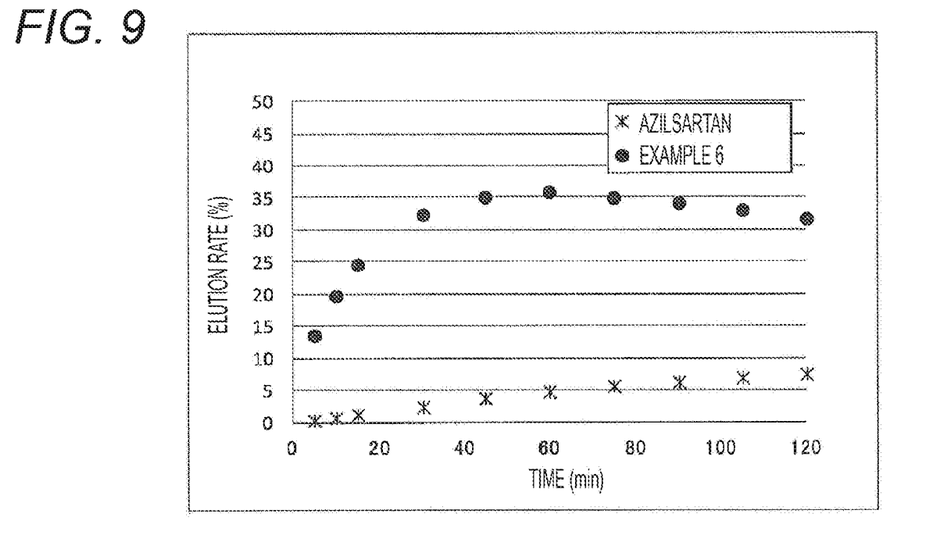
FIG. 9 shows the result of the elution test in the elution test solution No. 1 (pH 1.2) of the present active pharmaceutical ingredient carrier including azilsartan carried and an azilsartan crystal (azilsartan).

The results are shown in Table 5 and FIG. 9.

TABLE 5

| | | Elution rate (%) | | |
|---|---|---|---|---|
| | | 10 min | 60 min | 120 min |
| Example 5 | Elution test | 19.6 | 35.8 | 31.6 |
| AZL crystal | solution No. 1 (pH 1.2) | 0.58 | 4.7 | 7.4 |

The invention claimed is:

1. An active pharmaceutical ingredient carrier comprising:
   silica having a volume of a pore with a pore radius of 1 to 100 nm determined by BJH method of 3.0 to 5.0 ml/g, and a peak of a pore radius of 13 to 50 nm determined by BJH method; and
   an active pharmaceutical ingredient carried by the silica.

2. The active pharmaceutical ingredient carrier according to claim 1, wherein a volume of a pore with a pore radius in a range of 10 to 50 nm in the silica occupies 60% or more of a total pore volume.

3. The active pharmaceutical ingredient carrier according to claim 1, wherein the silica is hydrophilic.

4. The active pharmaceutical ingredient carrier according to claim 1, wherein the active pharmaceutical ingredient carried by the active pharmaceutical ingredient carrier is amorphous.

5. A method of producing an active pharmaceutical ingredient carrier, comprising the step of:
   dissolving an active pharmaceutical ingredient in an organic solvent, then adding silica, and removing the organic solvent,
   wherein the silica has a volume of a pore with a pore radius of 1 to 100 nm determined by BJH method of 3.0 to 5.0 ml/g, and a peak of a pore radius of 10 to 50 nm determined by BJH method.

* * * * *